United States Patent
Ding et al.

(10) Patent No.: US 8,853,221 B2
(45) Date of Patent: Oct. 7, 2014

(54) COMPOUNDS OF ESTROGEN-RELATED RECEPTOR MODULATORS AND THE USES THEREOF

(75) Inventors: Ke Ding, Guangzhou (CN); Chiwai Wong, Guangzhou (CN); Lijie Peng, Guangzhou (CN); Zhanfang Kang, Guangzhou (CN); Xi Zhou, Guangzhou (CN)

(73) Assignee: Guangzhou Institute of Biomedicine & Health, Chinese Academy of Sciences, Guangzhou (CN)

( * ) Notice: Subject to any disclaimer, the term of this patent is extended or adjusted under 35 U.S.C. 154(b) by 549 days.

(21) Appl. No.: 13/054,664

(22) PCT Filed: Mar. 6, 2009

(86) PCT No.: PCT/CN2009/000243
§ 371 (c)(1),
(2), (4) Date: May 20, 2011

(87) PCT Pub. No.: WO2010/006496
PCT Pub. Date: Jan. 21, 2010

(65) Prior Publication Data
US 2011/0218196 A1 Sep. 8, 2011

(30) Foreign Application Priority Data
Jul. 18, 2008 (CN) .......................... 2008 1 0029586

(51) Int. Cl.
*A01N 43/90* (2006.01)
*A61K 31/519* (2006.01)
*C07D 239/70* (2006.01)
*C07D 471/04* (2006.01)

(52) U.S. Cl.
CPC .................................. *C07D 471/04* (2013.01)
USPC ....................................... 514/259.4; 544/282

(58) Field of Classification Search
USPC ....................................... 514/259.4; 544/282
See application file for complete search history.

(56) References Cited

U.S. PATENT DOCUMENTS

| | | | |
|---|---|---|---|
| 3,169,129 A | 2/1965 | Rodgers et al. |
| 3,231,572 A | 1/1966 | Hayao |
| 3,268,529 A | 8/1966 | Bolger |
| 3,929,787 A | 12/1975 | Yale |
| 4,379,788 A | 4/1983 | Heider et al. |
| 4,431,440 A | 2/1984 | Bhalia et al. |
| 5,147,875 A | 9/1992 | Coates et al. |
| 5,756,510 A | 5/1998 | Griffin et al. |
| 5,783,577 A | 7/1998 | Houghten et al. |
| 5,922,866 A | 7/1999 | Miyata et al. |
| 5,948,775 A | 9/1999 | Koko et al. |
| 6,156,739 A | 12/2000 | Griffin et al. |
| 6,277,858 B1 | 8/2001 | Walter |
| 6,479,499 B1 | 11/2002 | Kuo et al. |
| 2003/0220227 A1 | 11/2003 | Gungor et al. |
| 2004/0041755 A1 | 3/2004 | Watanabe et al. |
| 2004/0110777 A1 | 6/2004 | Annis et al. |
| 2006/0012577 A1 | 1/2006 | Kyrola |
| 2006/0052345 A1 | 3/2006 | Shcherbakova et al. |
| 2007/0060601 A1 | 3/2007 | Arrington et al. |
| 2007/0065662 A1 | 3/2007 | Bennett et al. |
| 2008/0067219 A1 | 3/2008 | Barengo et al. |
| 2008/0188467 A1 | 8/2008 | Wong et al. |
| 2008/0194616 A1 | 8/2008 | Liu et al. |
| 2008/0275069 A1 | 11/2008 | Mizutani et al. |
| 2008/0293764 A1 | 11/2008 | Terakado et al. |
| 2011/0071148 A1 | 3/2011 | Ding et al. |

FOREIGN PATENT DOCUMENTS

| | | |
|---|---|---|
| CA | 1217768 A1 | 2/1987 |
| CA | 2278290 A1 | 8/1998 |
| EP | 0 054 132 A1 | 6/1982 |
| EP | 0 058 822 A1 | 9/1982 |
| EP | 0 518 033 A1 | 12/1992 |
| EP | 1 389 463 A1 | 2/2004 |
| EP | 1 757 594 A1 | 2/2007 |
| FR | 1 416 418 A | 11/1965 |
| GB | 2011410 A * | 7/1979 |
| JP | S61-254524 | 11/1986 |

(Continued)

OTHER PUBLICATIONS

Adams et. al., Journal of the American Chemical Society, 1952, American Chemical Society, vol. 74, pp. 5491-5497.*

(Continued)

*Primary Examiner* — Sarah Pihonak
(74) *Attorney, Agent, or Firm* — Saul Ewing LLP; Peter C. Lauro, Esq.

(57) ABSTRACT

The compounds according to formula (VIII), their pharmaceutically acceptable acid or base addition salts, and the uses thereof. These compounds and their pharmaceutically acceptable acid or base addition salts can be used for preparing medicaments for modulating estrogen related receptors (ERR), and treating metabolic diseases, such as high blood fat, fatty liver, hyperglycemia, diabetes, obesity. The substituents of the formula are defined in the description.

VIII

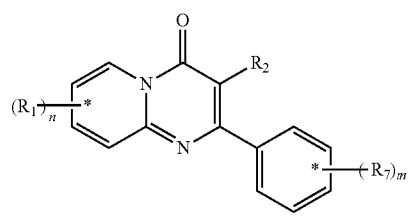

(VIII)

3 Claims, 5 Drawing Sheets

(56) References Cited

FOREIGN PATENT DOCUMENTS

| | | |
|---|---|---|
| JP | 2001-516749 | 10/2001 |
| JP | 2002-513394 | 5/2002 |
| JP | 2006-512315 | 4/2006 |
| WO | 97/08153 | 3/1997 |
| WO | 98/26664 | 6/1998 |
| WO | 98/26664 A1 | 6/1998 |
| WO | 9839332 | 9/1998 |
| WO | 02/48115 A2 | 6/2002 |
| WO | 2004/041755 A2 | 5/2004 |
| WO | 2005065183 A2 | 7/2005 |
| WO | 2005115993 A1 | 12/2005 |
| WO | 2006/012577 A2 | 2/2006 |
| WO | 20061012577 A2 | 2/2006 |
| WO | 2006116401 A1 | 11/2006 |

OTHER PUBLICATIONS

Crowley, Remington: The Science and Practice of Pharmacy, 2005, Lippincott Williams & Wilkins, 21$^{st}$ ed., p. 745.*

Form PCT/IPEA/409, WO, May 31, 2010, IPRP for PCT/CN2009/000234.

Form PCT/ISA/210, WO, Jun. 4, 2009, ISR for PCT/CN2009/000234.

Chemical Abstracts, 2006, vol. 144, CAN 144: 254092, CAS RN=877034-67-8.

Chemical Abstracts, 2000, vol. 132, CAN 132: 265188, CAS RN=263364-11-0.

Chemical Abstracts, 2000, vol. 132, CAN 132: 265187, CAS RN=263543-95-9.

Chemical Abstracts, 1999, vol. 130, CAN 130: 237551, CAS RN=221228-77-9, 221229-23-8, 221229-27-2.

Chemical Abstracts, 1998, vol. 128, CAN 128: 34772, CAS RN=199725-80-9.

Chemical Abstracts, 1976, vol. 84, CAN 84: 17264, CAS RN=54214-70-9, 54214-72-1.

Barnish et al., "Formation of 1,3-dianions of 2- and 3-acetamidopyridines by means of n-butyllithium. Condensations with carbonyl compounds and nitriles", The Journal of Organic Chemistry, vol. 33, No. 5, pp. 2116-2118 (1968).

Shur et al., "The Reaction of Amino Heterocycles with Reactive Esters. I. 2-Aminopyridines", Journal of Organic Chemistry, vol. 33, No. 8, pp. 3015-3020 (1968).

Yale, "9-Hydroxy-2-Methyl-4H-Pyridoul, 2-A 3/4 Pyrimidin-4-One 9-Hydroxy-2-Phenyl-4H-Pyridou1,2-A 3/4 Pyrimidin-4-One 9-Methy. -2-Phenyl-4-Pyridou1,2-A 3/4-Pyrimidin-4-one Ethyl 9-Hydroxy-4H-Pyridou1,2-A 3/4 Pyrimidin-4-One-3-Carboxylate and Their Derivatives", Journal of Heterocyclic Chemistry, vol. 12, No. 2, pp. 427-431 (1975).

Ferrarini et al., "Syntheses of Some Substituted Pyridou1,2-Alpha 3/4 Pyrimidin-4-ones and 1,8-Naphthyridines", Journal of Heterocyclic Chemistry, vol. 20, No. 4, pp. 1053-1057 (1983).

Chen et al., "Antitumor Agents. 174. 2',3',4',5,6,7-Substituted 2-Phenyl-1, 8-Napthtyridin-4-ones: Their Synthesis, Cytotoxicity, and Inhibition of Tubulin Polymerization", Journal of Medicinal Chemistry, vol. 40, No. 14., pp. 2266-2275 (1997).

Chen et al., "Antitumor Agents. 178. Synthesis and Biological Evaluation of Substituted 2-Aryl-1,8-Naphthyridin-4(1H)-ones as Antitumor Agents that Inhibit Tubulin Polymerization", Journal of Medicinal Chemistry, vol. 40, No. 19, pp. 3049-3056 (1997).

Ferrarini et al., "Condensation of substituted 2-aminopyridine with [beta]-ketocarboxylic esters: 4 H-pyrido [1,2- a ]pyrimidin-4-ones and pyridin-2-ones", Journal of Heterocyclic Chemistry, vol. 36, No. 5, pp. 1123-1127 (1999).

Ferrarini et al., "A novel class of highly potent and selective A1 adenosine antagonists: structure-affinity profile of a series of 1,8-naphthyridine derivatives", Journal of Medicinal Chemistry, vol. 43, No. 15, pp. 2814-2823 (2000).

Bonacorso et al., "New efficient approach for the synthesis of 2-alkyl(aryl) substituted 4 H—pyrido[1,2-a ]pyrimidin-4-ones", Journal of Heterocyclic Chemistry, vol. 43, No. 1, pp. 229-233 (2006).

La Motta et al., Pyrido[1,2- a ]pyrimidin-4-one Derivatives as a Novel Class of Selective Aldose Reductase Inhibitors Exhibiting Antioxidant Activity, Journal of Medicinal Chemistry, vol. 50, No. 20, pp. 4917-4927 (2007).

Kuninobu et al., "Isocyanate acting as a carbonyl precursor: pyridyl group-assisted formation of 4H-pyrido[1,2-a]pyrimidin-4-ones from ketimines and isocyanates", Organic & Biomolecular Chemistry, pp. 203-205 (2005).

Ariazi et al., "Estrogen-related receptors as emerging targets in cancer and metabolic disorders", Current Topics in Medicinal Chemistry, vol. 6, No. 3, pp. 203-215 (2006).

Supplementary European Search Report and European Search Opinion mailed Feb. 3, 2012, in corresponding European Patent Application No. 09797343.2.

Communication, European Patent Application No. 09719079.7, (Mar. 21, 2014).

Wang et al.,"Benign and Efficient Synthesis of 2-Substituted 4(3H)-quinazolinones Mediated by Iron(III) Chloride Hexahydrate in Refluxing Water", Bull. Chem. Soc. Jpn., vol. 79, No. 9, pp. 1426-1430 (2006).

Liu et al.,"Microwave-assisted one-pot synthesis of 2,3-disubstituted 3H-quinazolin-4-ones", Tetrahedron Letters, 2005, vol. 46, No. 8, pp. 1241-1244.

Snider et al., "Amine-Induced Rearrangement of 4-Imino-4H-3,I-Benz-Oxazines to 4-Quinazolinones Via Amidine Carboxamides", Heterocycles, 2003, vol. 61, pp. 173-182.

Rudolph et al., "Quinazolinone Derivatives as Orally Available Ghrelin Receptor Antagonist for the Treatment of Diabetes and Obesity", Journal of Medicinal Chemistry, 2007, vol. 50, No. 21, pp. 5202-5216.

Nielsen et al., "Phosphoramides. XIII.* Phosphorous Pentaoxide-Amine Hydrochloride Mixtures as Reagents in the Synthesis of 4(3H)-Quinazolinones and a 4-Quinazolinones", Acta Chemica Scandinavica, Series B: Organic Chemistry and Biochemistry, 1980, vol. B34, No. 9, pp. 634-642.

Barthelemy et al., "Parallel Fluorous Biphasic Synthesis of 3H-quinazolin-4-ones by an Aza-Wittig Reaction Employing Perfluoroalkyl-tagged Triphenylphosphine", Tetrahedron Letters, 43(2002), 807-810.

Rao et al., "Studies in the Formation of Heterocyclic Rings Containing Nitrogen: Part XXIX- Synthesis & Thermal Isomerization of 1-Alkyl-2-aryl-4(1H)-quinazolinones", Indian Journal of Chemistry, 1979, No. 6, vol. 18B, 493-496.

Notice of Reasons for Rejections mailed Apr. 23, 2013 in corresponding Japanese Application No. 2010-550017.

Chemical Abstracts, Nov. 16, 1984, CAS RN=1022-45-3.

Chemical Abstracts, Nov. 16, 1984, CAS RN=22686-81-3.

Chemical Abstracts, Nov. 16, 1984, CAS RN=59490-93-6.

Chemical Abstracts, Nov. 27, 1986, CAS RN=105493-92-3.

Office Action dated Aug. 14, 2012 issued in related Canadian Application No. 2,750,859.

\* cited by examiner

COMPOUNDS OF ESTROGEN-RELATED RECEPTOR MODULATORS AND THE USES THEREOF

This application is a U.S. National Phase of International Patent Application Serial No. PCT/CN2009/000243, filed Mar. 6, 2009, which claims priority to Chinese Patent Application No. CN 200810029586.9, filed Jul. 18, 2008.

FIELD OF THE INVENTION

This invention relates to small molecules which function as modulators of estrogen-related receptors.

BACKGROUND OF THE INVENTION

In recent years, the increasing incidences of metabolic diseases including obesity, diabetes, dyslipidemia, hypertension, and atherosclerosis, have led to higher risks of heart diseases, a leading cause of mortality worldwide. The healthcare cost associated with treatment is putting major burdens on the healthcare systems of developed as well as developing countries. Therefore, identifying novel targets and pharmacologic agents to treat and/or prevent these disorders are of high priorities.

Both type 1 (insulin-dependent diabetes mellitus, IDDM) and type 2 (noninsulin-dependent diabetes mellitus, NIDDM) diabetes are characterized by elevated levels of plasma glucose (hyperglycemia) in the fasting state or after administration of glucose during an oral glucose tolerance test. Insulin is the hormone that regulates glucose utilization by stimulating glucose and lipid metabolism in the main insulin-sensitive tissues including muscle, liver and adipose tissues. Inappropriate regulation of energy metabolism in these tissues accounts for most of the alterations in glucose homeostasis seen in patients with type 2 diabetes. In addition, patients having type 2 diabetes often have hyperinsulinemia (elevated plasma insulin levels). Insulin resistance, which means a resistance to the effect of insulin, plays an early role in the pathogenesis of type 2 diabetes.

Skeletal muscle and liver are both key insulin-responsive organs responsible for maintaining normal glucose homeostasis. Mitochondrial dysfunction has been closely associated with skeletal muscle insulin resistance in several studies. In skeletal muscle of human type II diabetics, the expression levels of mitochondrial oxidative phosphorylation (OX-PHOS) genes are reduced. The OXPHOS genes that are dysregulated in type II diabetic patients are under the transcriptional control of peroxisome proliferator-activated receptor □ coactivator-1□ (PGC-1α). The reduction of PGC-1α level will in theory induce the reduction of the OXPHOS genes and reduce the oxidation of fatty acids, and thus result in the reducing of lipid deposition in the skeletal muscle, and finally induce insulin resistance and type II diabetes. Actually, the imbalance of PGC-1α is a common phenomenon of prediabetics. This further proves that the reduction of PGC-1α level is an important factor inducing the diabetes.

Estrogen-related receptors (ERRs) are a kind of nuclear hormone receptor closely related to the estrogen receptor α. During the binding of the ERRs and their co-activator, no exogenous ligands and endogenous ligands participate, which is considered to construct constitutively active orphan nuclear hormone receptors. Studies show that ERRs include 3 kinds of different subtypes, i.e. ERRα, ERRβ and ERRγ (related documents: Giguere, V., Nature, 1988, 331, 91~94; Hong, H J. Biol. Chem. 1999, 274, 22618-22626; Heard, D. J. Mol. Endocrinol. 2000, 14, 382-392; Giguere, V. T. Trends. Endcrinol. Metab. 2002, 13(5), 220-225; etc.). ERRβ mainly relates to the upgrowth of organisms, and its expression is strictly controlled after birth, and there is a small amount of expression in the liver, stomach, skeletal muscle, heart and kidney. The expression of ERRγ mainly lies in the spinal cord and the centra nervous system. ERRα mainly exists in metabolically active tissues or organs such as skeletal muscle, heart, kidney and adipose tissue (related documents: Giguere, V., *Nature,* 1988, 331, 91~94; Sladek, R. *Mol. Cell. Biol.* 1997, 17, 5400~5409; etc.), and the interaction of ERRα and PGC-1 (peroxisome proliferator activated receptor γ (PPAR-γ) coactivator 1) controls the transcription of mitochondrial oxidative phosphorylation (OXPHOS) genes and regulates the material and energy metabolism of glucose and adipose (related documents: Schreiber, S. N. Proc. Natl. Acad. Sci. U.S.A. 2004, 101, 6472~6477; Schreiber, S. N. J. Biol. Chem. 2003, 278, 9013~9018; Huss, J. M. J. Biol. Chem. 2002, 277, 40265-40274; Ichida, M.; Nemoto, S. J. Biol. Chem. 2002, 277, 50991-50995; etc.).

The OXPHOS is the most crucial step during the ATP energy generating by material metabolism of the glucose, adipose, etc. PGC-1 is an important regulator of the OXPHOS and plays an important regulation role during the heat generation in the tissues such as skeletal muscle and brown adipose, and respiration and mitochondrial biogenesis in the muscle cell, and the transition of skeletal muscle fiber. Furthermore, PGC-1 also controls the expression of genes for encoding many kinds of gluconeogenic enzymes (related documents: Mootha, V. K. Nat. Genet. 2003, 34, 267-273; Patti, M. E. Proc. Natl. Acad. Sci. USA 2003, 100, 8466-8471; Puigserver, P. Endocr. Rev. 2003, 24, 78-90). Studies show that the reduction of PGC-1 may affect the metabolism of energy materials such as glucose and adipose, and induce excess blood glucose and lipid deposition in the skeletal muscle, and finally induce insulin resistance and type II diabetes.

ERRα is the direct downstream target gene of PGC-1α. The direct interaction of ERRα and PGC-1α controls the transcription of genes such as OXPHOS and fatty acid oxidase so as to regulate the process of OXPHOS (Mootha, V. K. Proc. Natl. Acad. Sci. U.S.A. 2004, 101, 6570-6575). Studies show that under the stimulation of environment signals such as fasting, physical training and cold, PGC-1α may facilitate the expression of ERRα, and further facilitate the transcription of ERRα by way of binding with ERRα to induce ERRα to bind with the specific binding site of gene promoter of itself. The interaction between the PGC-1α and ERRα can further promote the binding of ERRα with the other downstream gene promoters of PGC-1α, and facilitate the transcription of these downstream functional genes (such as phosphoenolpyruvate carboxykinase (PEPCK), medium chain acyl dehydrogenase (MCAD), and pyruvate dehydrogenase kinase 4 (PDK4)), and thus control the OXPHOS and the fatty acid oxidation effectively and promote the metabolism of fatty acid and glucose (FIG. 1A) (related documents: Schreiber, S. N. et al. Proc. Natl. Acad. Sci. U.S.A. 2004, 101, 6472~6477. Willy, P. J.; et al, Proc. Natl. Acad. Sci. U.S.A. 2004, 101, 8912~8917, etc.)

Therefore, with small molecular compounds especially small molecular promoter ERRα regulates the function of ERRα and PGC-1α, the function of OXPHOS genes is effectively improved, the oxidization of fatty acid is facilitated or the utilization of glucose is reduced, and it can be used as an effective way to cure diabetes and the related obesity, hyperglycemia, low blood glucose tolerance, insulin resistance, hyperlipidemia, lipid disorders, high blood cholesterol, high triglyceride, hypercholesteraemia, low high-density lipoprotein cholesterol levels, high low-density lipoprotein level, atherosclerosis, and its secondary disease, narrow blood vessels, abdominal obesity, metabolic syndrome and fatty liver. Furthermore, since the small molecular promoter ERRα can improve the expression of PGC-1α gene and increase the sensitivity of insulin. Therefore, they can also be used with other insulin sensitizer or insulin secretagogues to improve the clinical effect.

In addition, reduction of estrogen levels in post-menopausal results in an increase of bone loss leading to osteoporosis. Over-expression of ERRα in osteoblasts increases bone nodule formation, while reducing the expression by antisense results in a decrease of bone nodule formation. Therefore, compounds that enhance the activity of estrogen related receptors (ERRα, β, and γ, etc.) activity may have an anabolic effect for the regeneration of bone density. Conversely, with respect to bone diseases that are a result of abnormal bone growth, compounds that will interact with estrogen related receptors (ERRα, β, and γ) and decrease its biological activity may provide a benefit for the treatment of these diseases by retarding bone growth.

Although estrogen related receptors alpha, beta and gamma (ERRα, ERRβ and ERRγ) are considered to be orphan nuclear hormone receptors that display constitutively active transcriptional activities, synthetic phenolic acyl hydrazones have recently been demonstrated to be selective ERRβ and ERRγ agonists through binding to the C-terminally located ligand binding domain (LBD) and activating its function. However, no definitive ERR α agonist has been identified so far that would improve insulin resistance through enhancing the function of PGC1.

SUMMARY OF THE INVENTION

It is an object of the present invention to provide compounds as the estrogen-related receptor modulators.

In an embodiment, this invention provides compounds having formula VIII and their pharmaceutical acceptable salts and stereo isomers:

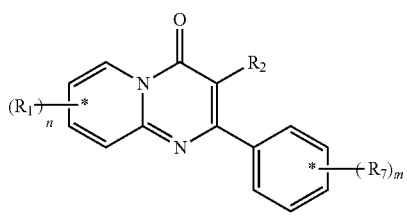

VIII wherein,
m is 0, 1 or 2;
n is 0, 1 or 2;
in the following, a is 0 or 1, b is 0 or 1;
$R_1$ and $R_7$ are independently selected from:
1) H;
2) Halo;
3) OH;
4) $(C=O)_a O_b C_1 \sim C_4$ alkyl;
5) $(C=O)_a O_b C_3 \sim C_6$ cycloalkyl;
$R_2$ is selected from:
1) H;
2) $C_1 \sim C_3$ alkyl;
3) $C_3 \sim C_6$ cycloalkyl;
the alkyl metioned above can be substituted by 0, 1 or more substituted groups independently selected from $R_4$ $R_4$ is selected from:
1) H;
2) $C_3 \sim C_6$ heterocyclyl.

The invention also provides a pharmaceutical composition containing any one of the compounds mentioned above or their pharmaceutically acceptable salts or pro-drugs thereof. The pharmaceutical composition can be used as a new class of therapeutics for the treatment of metabolic diseases.

The present invention relates to the use of the compounds mentioned above and their pharmaceutical acceptable salts which function as modulators of estrogen-related receptors as a new class of therapeutics for the treatment of metabolic diseases.

Preferably, the metabolic diseases includes: (1) Type II diabetes; (2) hyperglycemia; (3) reduced glucose tolerance; (4) insulin resistance; (5) obesity; (6) hyperlipidemia; (7) hypertriglyceridemia; (8) hypercholesterolemia; (9) low levels of HDL; (10) high levels of LDL; (11) atherosclerosis; (12) vascular restenosis; (13) fatty liver.

The present invention provides compounds represented by Formula VIII, which are agonists of estrogen-related receptors (ERRα, β, and γ, etc). The invention also relate to the use of compounds of the invention to treat a subject suffering from or diagnosed with metabolic diseases like Type II diabetes and associated hyperlipidemia, hypertriglyceridemia, hypercholesterolemia, obesity and fatty liver.

The present invention contemplates that compounds which agonize the functions of ERRα and its interacting partner PGC-1α will alleviate the extent of insulin resistance, improve glucose homeostasis in diabetic patients and restore insulin sensitivity. The present invention contemplates these compounds may reduce blood glucose levels and diabetic serum marker hemoglobin A1c glycosylation level. Furthermore, the present invention contemplates that ERRα agonists may enhance the therapeutic effects of current and developing insulin sensitizers and insulin secertagogues when used in combination.

DETAILED DESCRIPTION OF THE PREFERRED EMBODIMENT

Figure 1:
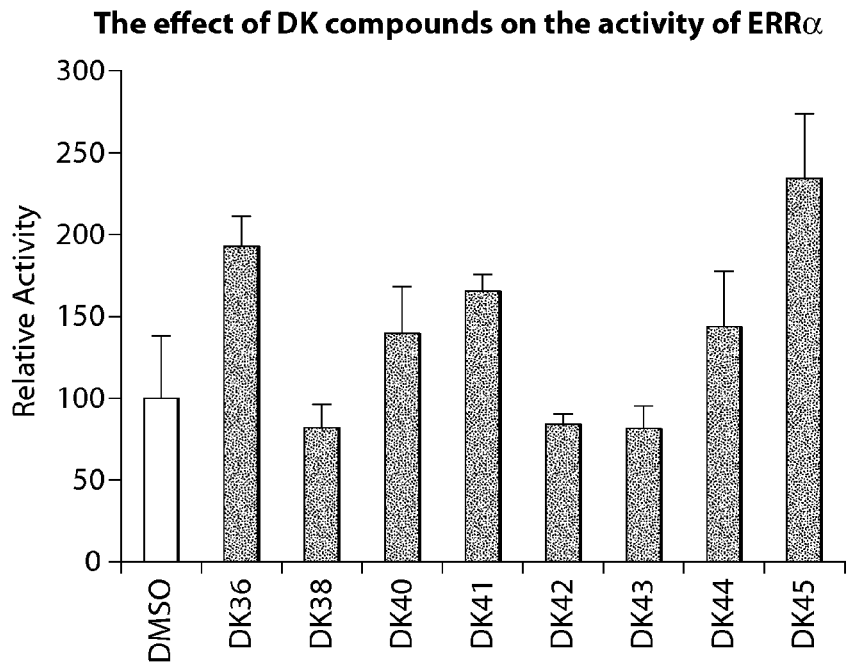
FIG. 1 is a diagram showing the effect of DK compounds on the activity of ERRα.

The compounds related to the invention could have chiral center, chiral axis or chiral surface. They may have racemate. All the stero isomers, racemate mixtures and other isomers are included in the invention. The compounds related to the invention may have tautomers. Although there is only one taumoter is descripted, the invention included all the possible taumoters.

In this invention, the term "alkyl" and "sub-alkyl" means a ranched-chain or straight chain alkyl group with certain number of carbon atoms. For example, the "$C_1$-$C_8$" in "$C_1$-$C_8$ alkyl" is defined to straight-chain or branched-chain alkyl group with 1, 2, 3, 4, 5, 6, 7 or 8 carbon atoms. "$C_1$-$C_8$ alkyl" includes methyl, ethyl, n-propyl, isopropyl, n-butyl, tert-butyl, isobutyl, pentyl, hexyl, heptyl-, octyl, etc. The term "cycloalkyl" refers to a specific single saturated ring alkyl with certain number of carbon atoms. For examples, "cycloalkyl" includes cyclopropyl-, methyl-cyclopropyl-, 2,2-dimethyl-cyclobutyl, 2-ethyl-cyclopentadienyl-, cyclohexyl etc.

"Alkoxy" means a substituent connecting certain number of carbon atoms of the cyclic alkyl or noncyclic alkyl group through oxygen atom.

"Heterocycle" is an aromatic or nonaromatic ring containing 5~10 atoms, in which contains 1~4 hetero atoms such as O, N, S. "Heterocycle" includes the hetero aromatic ring as mentioned above, it also includes dihydro and tetrahydro analogs. "Heterocycles" include but not limit to: benzimidazolyl, benzo furyl, benzopyranyl, benzo pyrazolyl, benzotriazolyl, benzo thienyl, benzoxazolyl, carbazolyl, carbolinyl, miso-phenanthrolinyl, furyl, imidazolyl, dihydro-indolyl, indolyl, indolazinyl, indazolyl, furans isobenzofuranyl, isoquinolinyl, isothiazolyl, isoxazolyl, Chennai pyridyl, oxadiazolyl, oxazolyl, oxazolinyl, isoxazole morpholinyl, oxetanyl, pyranyl, pyrazinyl, pyrazolyl, pyridazinyl, pyridazinyl, pyridyl, pyrimidinyl, pyrrolyl, quinazolinyl, quinolyl, tetrahydro pyranyl, tetrazolyl, pyridyl tetrazolyl, thiadiazolyl, thiazolyl, thienyl, triazolyl, I, 4-alkyl-dioxinyl, hexallydroazepinyl, piperazinyl, piperidinyl, pyridine-2-keto, alkyl pyrrolidinyl, morpholinyl, thiomorpholinyl, dihydro-benzimidazolyl, dihydro-benzo furyl, benzo-dihydro-thienyl, dihydro-benzoxazolyl, dihydro-furyl, dihydro-benzimidazolyl, dihydro-indolyl, dihydro-isoxazolyl, dihydro-iso thiazolyl, dihydro-oxadiazolyl, dihydro-oxazolyl, dihydro-pyrazinyl, dihydro-pyrazolyl, dihydro pyridyl, dihydro-pyrimidinyl, dihydro-pyrrolyl, dihydrofolate quinolyl, tetrazolyl dihydro, dihydro-thiadiazolyl, dihydro thiazolyl, dihydro thienyl, dihydro-triazolyl, methylene dioxy benzophenone acyl and their N-oxides, etc. The connection of the heterocyclic ring substitutent is realized by carbon atom or hetero-atom.

In one embodiment, heterocycle is selected as benzimidazolyl, imidazolyl, 2-imidazoline ketone, indole-based, isoquinolinyl, morpholinyl, piperidinyl, piperazinyl, pyridyl, alkyl pyrrole, 2-piperidine ketone, 2-pyrimidine ketone, 2-pyrrolidone, quinolyl, tetrahydrofuranyl, tetrahydro isoquinolinyl, thienyl, etc.

As it can be easily understood, halides used in the invention include fluoride, clorine, fluorine, bromine and iodine.

In an embodiment, $R_4$ may form a mono ring containing 4~7 atoms or a bicyclic ring in which each ring comprises 4~7 atoms through the N, atom which connects R5 and R6. The mono ring or bicyclic ring may further comprises 1~2 hetero atoms selected as N, O, S. The mono ring or bicyclic ring can also be substituted by 1 or more sunstituents selected as $R_5$. The hetero cyclic rings formed include but not limit to the following heterocycles:

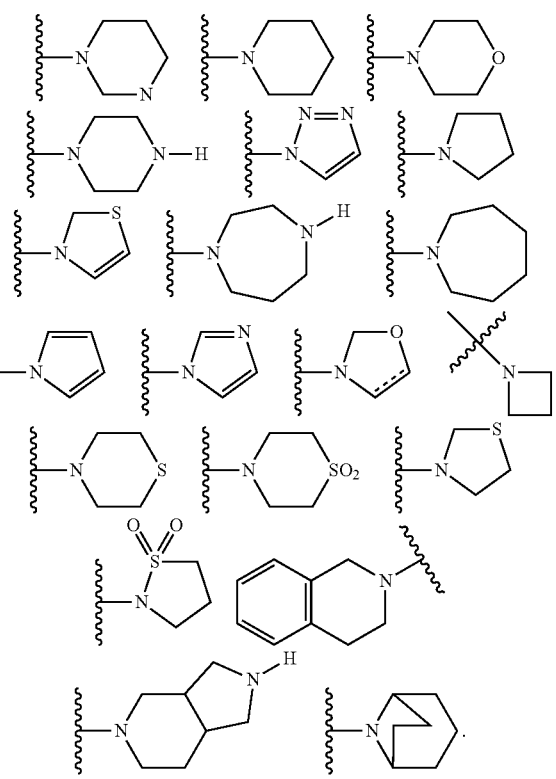

In one embodiment, $R_1$ is selected as halogen, hydroxy, ($C_1$-$C_6$) alkyl, or alkoxy.

In one embodiment, $R_2$ is selected as H, alkyl, or alkyl group substituted by $R_5$.

In one embodiment, a is 0, b is 1. In another embodiment, a is 0, b is 0.

The invention includes the free forms of compounds with formula VIII and also the pharmaceutical acceptable salts or stero isomers of formula VIII. In one embodiment, the special examples in the invention are the protonated salts of amines. The "free form" means amines which do not form salts with acids. "Pharmaceutical acceptable salts" include all the salt forms of Formula VIII.

"Pharmaceutical acceptable salts" in the invention mean the salts formed by the basic compounds in the invention with normal nontoxicic organic acids and inorganic acids. The acids include but not limit to: hydrochloric acid, hydrobromic acid, sulfuric acid, sulfamic acid, phosphoric acid, nitric acid, acetic acid, propionic acid, succinic acid, glycolic acid, stearic acid, lactic acid, malic acid, tartaric acid, lemon acid, ascorbic acid, bashing acid, maleic acid, hydroxy-maleic acid, phenylacetic acid, glutamic acid, benzoic acid, salicylic acid, sulfanilic acid, 2-acetoxy-benzoic acid 1, p-toluenesulfonic acid, methanesulfonic acid, ethane disulfonic, oxalic acid, hydroxyethyl sulfonic acid, trifluoroacetic acid, etc.

If the related compounds are acids, "pharmaceutical acceptable salts" mean the salts formed by the acidic compounds in the invention with normal nontoxicic organic bases or inorganic bases. The salts formed by acidic compounds with inorganic bases include but not limited to: aluminum salt, ammonium salt, calcium salt, copper salt, iron salt, ferrous salt, lithium salt, magnesium salt, manganese salt, manganese sub-salt, potassium, sodium, zinc, etc. ammonium salt, calcium salt, magnesium salt, potassium salt and sodium salt are preferred. The organic bases include but not limited to: primary amine, secondary amine, tertiary amine salts, substituted amines including naturally occurring substituted amines, cyclic amines and basic ion exchange resins such as arginine, betaine, caffeine, choline, N,N'-dibenzyl-ethylenediamine, diethylamine, 1,2 diethyl amino alcohol, dimethyl amino ethanol, amino-ethanol, ethanolamine, ethylenediamine, N-ethyl morpholine, N-ethyl piperidine, glucose amine, glucosamine, histidine, hydroxyproline cobalt amine, isopropyl amine, lysine, methyl-glucosamine, morpholine, piperazine, piperidine, polyamine resins, procaine, purine, pentoxifylline, triethyl amine, trimethyl amine, tripropyl amine, tromethamine, etc.

The related compounds can be prepared by using the following method. Of note, the synthetic scheme only outlines the examples. The related compounds may have more different substituents and can be made by other methods.

As shown in the scheme, compound 3 was synthesized according to the following procedure: 2-aminopyridine (1.00 mmol) and the suitable β-keto ester (1.50 mmol) in PPA (2.00 g) was heated at 130□ with frequent stirring. After 4 h, the reaction mixture was cooled in ice bath and neutralized with 5% aqueous sodium hydroxide to allow pH>7. The solid precipitate was collected by filtration, washed with water, and recrystallized.

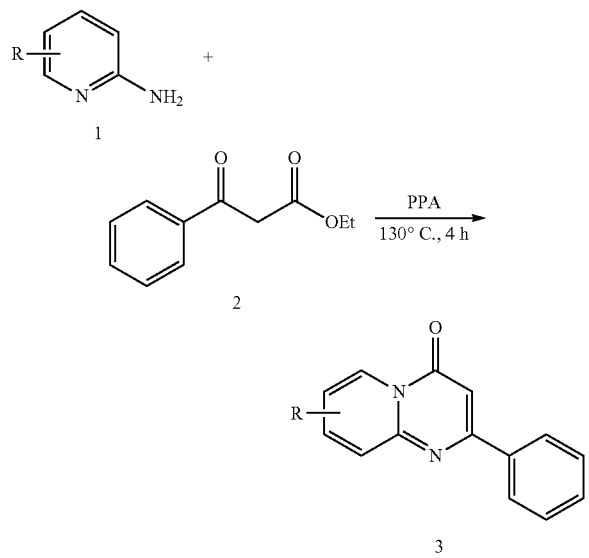

The present invention contemplates that compounds which agonize the function of ERRs, especially agonists or partial agonists of ERRα. Some compounds can functionally stimulate the functions of both ERRα and ERRβ and consider ERRα/β dual agonists. Some compounds can functionally stimulate the functions of both ERRα and ERRγ and consider ERRα/γ dual agonists. Some compounds can functionally stimulate the functions of both ERRα ERRβ and ERRγ and consider ERRα/β/γ pan-agonists. The invention also relate to the use of compounds of the invention to treat a subject suffering from or diagnosed with a disease, disorder, or medical condition mediated by estrogen-related receptors.

The present invention contemplates that compounds which agonize the functions of ERRα and its interacting partner PGC-1α will alleviate the extent of insulin resistance, improve glucose homeostasis in diabetic patients and restore insulin sensitivity. The present invention contemplates these compounds may reduce blood glucose levels and diabetic serum marker hemoglobin A1c glycosylation level. The present invention provides kits comprising compounds or their pharmaceutical acceptable salts for administering to an animal or patients with symptoms of type II diabetes.

In one embodiment, this present invention provides a method of using ERR modulators for treatment of type II diabetes.

In another embodiment, this present invention provides a method of using compounds with Formula VIII or their pharmaceutical acceptable salts for treatment of patients or animals with related diseases.

In another embodiment, this present invention provides a method of using compounds mentioned or their pharmaceutical acceptable salts for treatments of diseases related to ERR including but not limited to: (1) Type II diabetes; (2) hyperglycemia; (3) reduced glucose tolerance; (4) insulin resistance; (5) obesity; (6) hyperlipidemia; (7) hypertriglyceridemia; (8) hypercholesterolemia; (9) low levels of HDL; (10) high levels of LDL; (11) atherosclerosis; (12) vascular restenosis; (13) fatty liver.

In another embodiment, this present invention relates to compounds or their pharmaceutical acceptable salts for treatments of osteoporosis or related diseases.

In another embodiment, this present invention provides a method of using compounds mentioned or their pharmaceutical acceptable salts for treatments of hyperglycemia, atherosclerosis, low HDL levels, high LDL levels, hyperlipidemia, hypertriglyceridemia, etc.

The compound may be used alone or advantageously may be administered with a cholesterol biosynthesis inhibitor, particularly an HMG-CoA reductase inhibitor such as lovastatin, simvastatin, rosuvastatin, pravastatin, fluvastatin, atorvastatin, rivastatin, itavastatin, or ZD-4522. The compound may also be used advantageously in combination with other lipid lowering drugs such as cholesterol absorption inhibitors (for example stanol esters, sterol glycosides such as tiqueside, and azetidinones such as ezetimibe), ACAT inhibitors (such as avasimibe), CETP inhibitors, niacin, bile acid sequestrants, microsomal triglyceride transport inhibitors, and bile acid reuptake inhibitors. These combination treatments may also be effective for the treatment or control of one or more related conditions selected from the group consisting of hypercholesterolemia, atherosclerosis, hyperlipidemia, hypertriglyceridemia, high LDL levels, low HDL levels, etc.

Another aspect of the invention provides a method of treating inflammatory conditions, including inflammatory bowel disease, Crohn's disease, and ulcerative colitis by administering an effective amount of a compound of this invention to a patient in need of treatment. Additional inflammatory diseases that may be treated with the instant invention include gout, rheumatoid arthritis, osteoarthritis, multiple sclerosis, asthma, ARDS, psoriasis, vasculitis, ischemia/reperfusion injury, frostbite, and related diseases.

The compounds as defined herein may be used to treat diseases according to the following methods, as well as other diseases not listed below:

(1) A method for treating non-insulin dependent diabetes mellitus (type 2 diabetes) in a human or other mammalian patient in need of such treatment which comprises administering to the patient a therapeutically effective amount of a compound of Formula VIII;

(2) A method for treating or controlling hyperglycemia in a human or other mammalian patient in need of such treatment which comprises administering to the patient a therapeutically effective amount of a compound of Formula VIII;

(3) A method for treating or controlling obesity in a human or other mammalian patient in need of such treatment which comprises administering to the patient a therapeutically effective amount of a compound of Formula VIII;

(4) A method for treating or controlling hypercholesterolemia in a human or other mammalian patient in need of such treatment which comprises administering to the patient a therapeutically effective amount of a compound of Formula VIII;

(5) A method for treating or controlling hypertriglyceridemia in a human or other mammalian patient in need of such treatment which comprises administering to the patient a therapeutically effective amount of a compound of Formula VIII;

(6) A method for treating or controlling one or more lipid disorders, including low HDL cholesterol, high LDL cholesterol, hyperlipidemia, hypercholesterolemia, and hypertriglyceridemia in a human or other mammalian patient in need of such treatment which comprises administering to the patient a therapeutically effective amount of a compound of Formula VIII;

(7) A method for reducing the risks of adverse sequelae associated with metabolic syndrome in a human or other mammalian patient in need of such treatment which comprises administering to the patient a therapeutically effective amount of a compound of Formula VIII; and (8) A method for treating atherosclerosis, for reducing the risk of developing atherosclerosis, for delaying the onset of atherosclerosis, and/or reducing the risk of sequelae of atherosclerosis in a human or other mammalian patient in need of such treatment or at risk of developing atherosclerosis or sequelae of atherosclerosis, which comprises administering to the patient a therapeutically effective amount of a compound of Formula VIII. Sequelae of atherosclerosis include for example angina, claudication, heart attack, stroke, etc.

Administration and Dose Ranges

Any suitable route of administration may be employed for providing a mammal, especially a human, with an effective dose of a compound of the present invention. For example, oral, rectal, topical, parenteral, ocular, pulmonary, nasal, and the like may be employed. Dosage forms include tablets, troches, dispersions, suspensions, solutions, capsules, creams, ointments, aerosols, and the like. Preferably compounds of Formula VIII are administered orally.

The effective dosage of active ingredient employed may vary depending on the particular compound employed, the mode of administration, the condition being treated and the severity of the condition being treated. Such dosage may be ascertained readily by a person skilled in the art.

When treating or controlling diabetes mellitus and/or hyperglycemia or hypertriglyceridemia or other diseases for which compounds of Formula VIII are indicated, generally satisfactory results are obtained when the compounds of the present invention are administered at a daily dosage of from about 0.1 milligram to about 500 milligram per kilogram of animal body weight, preferably given as a single daily dose or in divided doses two to four times a day, or in sustained release form. For most large mammals, the total daily dosage is from about 0.1 milligrams to about 1500 milligrams, preferably from about 0.5 milligram to about 100 milligrams. In the case of a 70 kg adult human, the total daily dose will generally be from about 1 milligram to about 500 milligrams. For a particularly potent compound, the dosage for an adult human may be as low as 0.1 mg. The dosage regimen may be adjusted within this range or even outside of this range to provide the optimal therapeutic response.

Oral administration will usually be carried out using tablets. Examples of doses in tablets are 0.1 mg, 0.2 mg, 0.25 mg, 0.5 mg, 1 mg, 2 mg, 5 mg, 10 mg, 25 mg, 50 mg, 100 mg, and 250 mg. Other oral forms can also have the same dosages (e.g. capsules).

Pharmaceutical Compositions

Another aspect of the present invention provides pharmaceutical compositions which comprise a compound of Formula VIII and a pharmaceutically acceptable carrier. The pharmaceutical compositions of the present invention comprise a compound of Formula VIII or a pharmaceutically acceptable salt as an active ingredient, as well as a pharmaceutically acceptable carrier and optionally other therapeutic ingredients. The term "pharmaceutically acceptable salts" refers to salts prepared from pharmaceutically acceptable non-toxic bases or acids including inorganic bases or acids and organic bases or acids. A pharmaceutical composition may also comprise a pro-drug, or a pharmaceutically acceptable salt thereof, if a prodrug is administered.

The compositions include compositions suitable for oral, rectal, topical, parenteral (including subcutaneous, intramuscular, and intravenous), ocular (ophthalmic), pulmonary (nasal or buccal inhalation), or nasal administration, although the most suitable route in any given case will depend on the nature and severity of the conditions being treated and on the nature of the active ingredient. They may be conveniently presented in unit dosage form and prepared by any of the methods well-known in the art of pharmacy.

In practical use, the compounds of Formula VIII can be combined as the active ingredient in intimate admixture with a pharmaceutical carrier according to conventional pharmaceutical compounding techniques. The carrier may take a wide variety of forms depending on the form of preparation desired for administration, e.g., oral or parenteral (including intravenous). In preparing the compositions for oral dosage form, any of the usual pharmaceutical media may be employed, such as, for example, water, glycols, oils, alcohols, flavoring agents, preservatives, coloring agents and the like in the case of oral liquid preparations, such as, for example, suspensions, elixirs and solutions; or carriers such as starches, sugars, microcrystalline cellulose, diluents, granulating agents, lubricants, binders, disintegrating agents and the like in the case of oral solid preparations such as, for example, powders, hard and soft capsules and tablets, with the solid oral preparations being preferred over the liquid preparations.

Because of their ease of administration, tablets and capsules represent the most advantageous oral dosage unit form in which case solid pharmaceutical carriers are obviously employed. If desired, tablets may be coated by standard aqueous or nonaqueous techniques. Such compositions and preparations should contain at least 0.1 percent of active compound. The percentage of active compound in these compositions may, of course, be varied and may conveniently be between about 2 percent to about 60 percent of the weight of the unit. The amount of active compound in such therapeutically useful compositions is such that an effective dosage will be obtained. The active compounds can also be administered intranasally as, for example, liquid drops or spray.

The tablets, pills, capsules, and the like may also contain a binder such as gum tragacanth, acacia, corn starch or gelatin; excipients such as dicalcium phosphate; a disintegrating agent such as coin starch, potato starch, alginic acid; a lubricant such as magnesium stearate; and a sweetening agent such as sucrose, lactose or saccharin. When a dosage unit form is a capsule, it may contain, in addition to materials of the above type, a liquid carrier such as fatty oil.

Various other materials may be present as coatings or to modify the physical form of the dosage unit. For instance, tablets may be coated with shellac, sugar or both. A syrup or elixir may contain, in addition to the active ingredient, sucrose as a sweetening agent, methyl and propylparabens as preservatives, a dye and a flavoring such as cherry or orange flavor.

Compounds of formula VIII may also be administered parenterally. Solutions or suspensions of these active compounds can be prepared in water suitably mixed with a surfactant such as hydroxypropylcellulose. Dispersions can also be prepared in glycerol, liquid polyethylene glycols and mixtures thereof in oils. Under ordinary conditions of storage and use, these preparations contain a preservative to prevent the growth of microorganisms.

The pharmaceutical forms suitable for injectable use include sterile aqueous solutions or dispersions and sterile powders for the extemporaneous preparation of sterile injectable solutions or dispersions. In all cases, the form must be sterile and must be fluid to the extent that easy syringability exists. It must be stable under the conditions of manufacture and storage and must be preserved against the contaminating action of microorganisms such as bacteria and fungi. The carrier can be a solvent or dispersion medium containing, for example, water, ethanol, polyol (e.g. glycerol, propylene glycol and liquid polyethylene glycol), suitable mixtures thereof, and vegetable oils.

Metabolites-Prodrugs

Therapeutically active metabolites, where the metabolites themselves fall within the scope of the claimed invention, are also compounds of the current invention. Prodrugs, which are compounds that are converted to the claimed compounds as they are being administered to a patient or after they have been administered to a patient, are also compounds of this invention.

Combination Therapy

Compounds of Formula VIII may be used in combination with other drugs that may also be useful in the treatment or amelioration of the diseases or conditions for which compounds of Formula VIII are useful. Such other drugs may be administered, by a route and in an amount commonly used therefore, contemporaneously or sequentially with a compound of Formula VIII. When a compound of Formula VIII is used contemporaneously with one or more other drugs, a pharmaceutical composition in unit dosage form containing such other drugs and the compound of Formula VIII is preferred. However, the combination therapy also includes therapies in which the compound of Formula VIII and one or more other drugs are administered on different overlapping schedules. It is also contemplated that when used in combination with one or more other active ingredients, the compound of the present invention and the other active ingredients may be used in lower doses than when each is used singly. Accordingly, the pharmaceutical compositions of the present invention include those that contain one or more other active ingredients, in addition to a compound of Formula VIII.

Examples of other active ingredients that may be administered in combination with a compound of Formula VIII, and either administered separately or in the same pharmaceutical composition, include, but are not limited to:

1) PPAR gamma agonists and partial agonists, including both glitazones and non-glitazones (e.g. troglitazone, pioglitazone, englitazone, MCC-555, rosiglitazone, balaglitazone, netoglitazone, T-131, LY-300512, and LY-818);

2) biguanides such as metformin and phenformin;

3) protein tyrosine phosphatase-IB (PTP-1B) inhibitors;

4) dipeptidyl peptidase IV (DP-IV) inhibitors;

5) insulin or insulin mimetics;

6) sulfonylureas such as tolbutamide and glipizide, or related materials;

7) α-glucosidase inhibitors (such as acarbose);

8) agents which improve a patient's lipid profile, such as (i) HMG-CoA reductase inhibitors (lovastatin, simvastatin, rosuvastatin, pravastatin, fluvastatin, atorvastatin, rivastatin, itavastatin, ZD-4522 and other statins), (ii) bile acid sequestrants (cholestyramine, colestipol, and dialkylaminoalkyl derivatives of a cross-linked dextran), (iii) nicotinyl alcohol, nicotinic acid or a salt thereof, (iv) PPARα agonists such as fenofibric acid derivatives (gemfibrozil, clofibrate, fenofibrate and bezafibrate), (v) cholesterol absorption inhibitors, such as for example ezetinibe, (vi) acyl CoA:cholesterol acyltransferase (ACAT) inhibitors, such as avasimibe, (vii) CETP inhibitors, and (viii) phenolic anti-oxidants, such as probucol;

9) PPARα/γ dual agonists, such as KRP-297, muraglitazar, tesaglitazar, farglitazar, and JT-501;

10) PPARδ agonists such as those disclosed in WO097/28149;

11) antiobesity compounds such as fenfluramine, dexfenfluramine, phentiramine, subitramine, orlistat, neuropeptide Y5 inhibitors, Mc4r agonists, cannabinoid receptor 1 (CB-1) antagonists/inverse agonists, and .beta.3 adrenergic receptor agonists;

12) ileal bile acid transporter inhibitors;

13) agents intended for use in inflammatory conditions such as aspirin, non-steroidal anti-inflammatory drugs, glucocorticoids, azulfidine, and cyclo-oxygenase 2 selective inhibitors;

14) glucagon receptor antagonists;

15) GLP-1 and its analogs, such as exenitide;

16) GLP-1 receptor agonists.

The above combinations include combinations of a compound of the present invention not only with one other active compound, but also with two or more other active compounds. Non-limiting examples include combinations of compounds having Formula VIII with two or more active compounds selected from biguanides, sulfonylureas, HMG-CoA reductase inhibitors, other PPAR agonists, PTP-1B inhibitors, DP-IV inhibitors, and anti-obesity compounds.

Example 1

8-methoxy-2-phenyl-4H-pyrido[1,2-a]pyrimidin-4-one

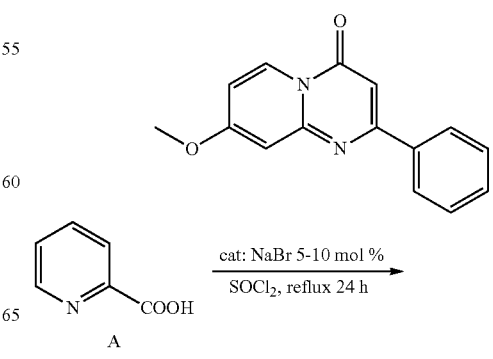

-continued

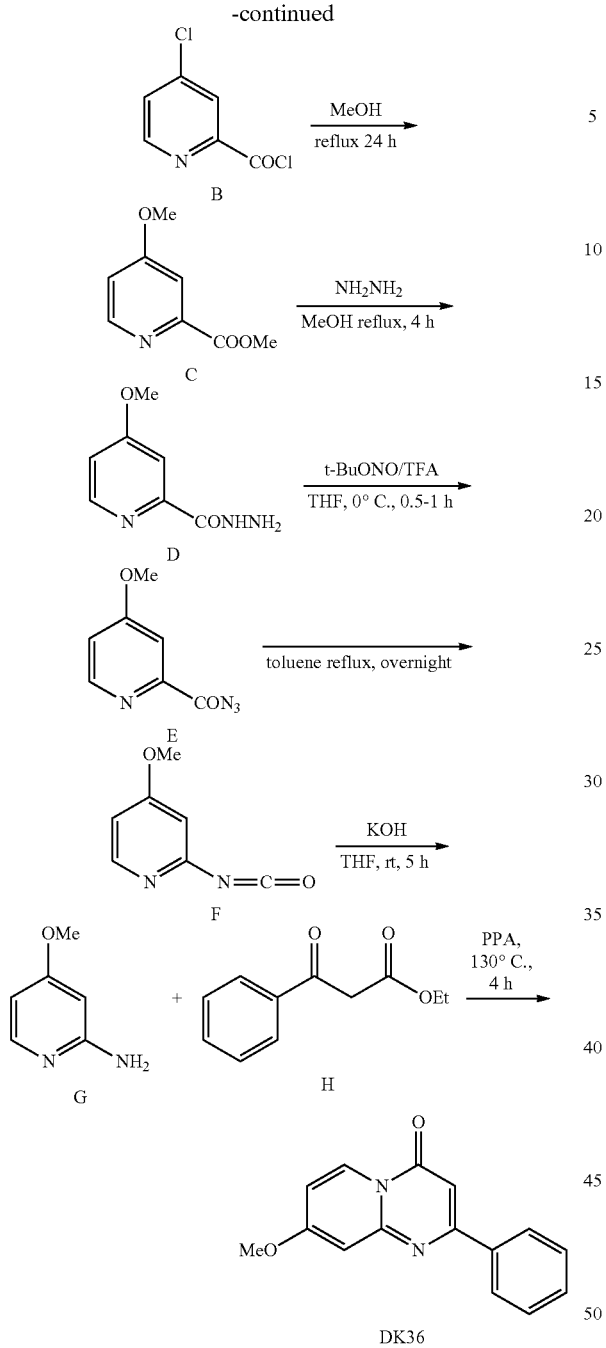

The solution of compound A and 5% mol sodium bromide in thionyl chloride was refluxed for 24 h, then the residual thionyl chloride was removed in vacuo to get compound B. compound B was added dropwisely mathanol at 0° C. the mixture was refluxed for 24 h, then the solvent was removed in vacuo. The residue was transferred into ethyl acetate and washed with saturated aqueous sodium bicarbonate, and brine. The solution was then dried over sodium sulfate, filtered, concentrated and purified by column chromatography to provide the desired compound C. Compound C in methanol was added hydrazine (1.5 eqiv), the mixture was refluxed for 4 h and then cooled to room temperature, filtrated to get compound D.

To an ice-bath solution of compound D in dry tetrahydrofuran was added dropwise trifluoroacetic acid (1.0 eqiv), followed by t-Butyl nitrite (3.0 eqiv), the mixture was continued to stirred for additional 30 min at the same temperature, then the solvent was removed to get the crude product compound E.

The solution of compound E in dry toluene was refluxed for overnight, then toluene was removed in vacuo. The residue was dissolved in tetrahydrofuran, and added aqueous potassium hydroxide (5.0 eqiv, 10 N). The reaction mixture was stirred at room temperature for 5 h, and then partitioned between dichloromethane and brine. The dichloromethane extracts were washed with brine, dried with sodium sulfate, and concentrated in vacuo. Purification by column chromatography to afforded compound G.

Compound G and H in polyphosphoric acid was heated to 130° C. for 4 h, then cooled to room temperature. The pH was adjusted to >7 with aqueous sodium hydroxide, and it was extracted with dichloromethane, washed with brine, dried with sodium sulfate, concentrated and purified by column chromatography to get final compound DK36 (example 1).

$^1$HNMR (400 MHz, CDCl$_3$), δ8.91 (d, J=8.0 Hz, 1H), 8.02~8.05 (m, 2H), 7.46~7.48 (m, 3H), 6.97 (d, J=2.8 Hz, 1H), 6.76 (dd, J=2.8, 8.0 Hz, 1H), 6.71 (s, 1H), 3.95 (s, 3H); MS(ESI), m/z: 253 (M+H)$^+$.

Example 2

8-methoxy-3-methyl-2-phenyl-4H-pyrido[1,2-a]pyrimidin-4-one

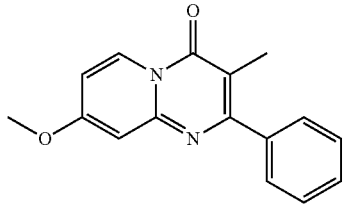

Synthetic route is the same as shown in Example 1.
MS(ESI), m/z: 267 (M+H)$^+$.

Example 3

8-hydroxy-2-phenyl-4H-pyrido[1,2-a]pyrimidin-4-one

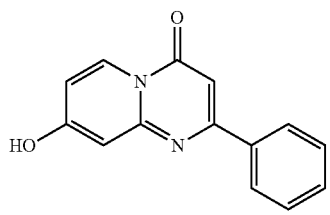 [SMILES: O=c1cc(-c2ccccc2)nc2cc(O)ccn12]

Synthetic route is the same as shown in Example 1.
$^1$HNMR (400 MHz, DMSO-$_{d6}$), δ9.02 (d, J=7.6 Hz, 1H), 8.15~8.16 (d, J=6.0 Hz, 2H), 7.67~7.69 (m, 3H), 7.14~7.17 (m, 2H), 6.80 (s, 1H);
MS(ESI), m/z: 239 (M+H)$^+$.

Example 4

8-ethoxy-2-phenyl-4H-pyrido[1,2-a]pyrimidin-4-one

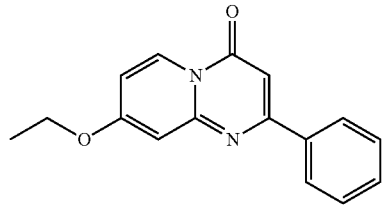 [SMILES: CCOc1ccn2c(=O)cc(-c3ccccc3)nc2c1]

Synthetic route is the same as shown in Example 1.

$^1$HNMR (400 MHz, DMSO-$_{d6}$), δ8.95 (d, J=7.6 Hz, 1H), 8.27~8.29 (m, 2H), 7.61~7.63 (m, 3H), 7.19 (d, J=2.4 Hz, 1H), 7.12 (dd, J=8.0, 2.8 Hz, 1H), 6.89 (s, 1H), 4.41 (q, J=6.8 Hz, 2H), 1.51 (t, J=6.8 Hz, 3H);

MS(ESI), m/z: 267 (M+H)$^+$.

Example 5

8-(allyloxy)-2-phenyl-4H-pyrido[1,2-a]pyrimidin-4-one

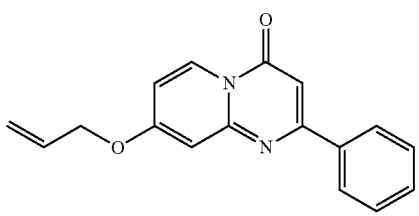 [SMILES: C=CCOc1ccn2c(=O)cc(-c3ccccc3)nc2c1]

Synthetic route is the same as shown in Example 1.

$^1$HNMR (400 MHz, DMSO-$_{d6}$), δ8.97 (d, J=7.6 Hz, 1H), 8.27~8.29 (m, 2H), 7.61~7.63 (m, 3H), 7.22 (d, J=2.0 Hz, 1H), 7.17 (dd, J=7.6, 2.0 Hz, 1H), 6.90 (s, 1H), 6.15~6.25 (m, 1H), 5.60 (d, J=17.2 Hz, 1H), 5.46 (d, J=10.4 Hz, 1H), 4.96 (d, J=5.2 Hz, 2H);

MS(ESI), m/z: 279 (M+H)$^+$.

Example 6

8-isopropoxy-2-phenyl-4H-pyrido[1,2-a]pyrimidin-4-one

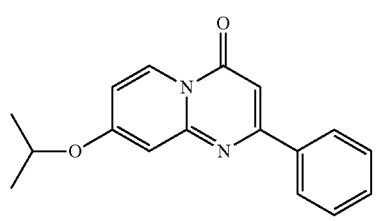 [SMILES: CC(C)Oc1ccn2c(=O)cc(-c3ccccc3)nc2c1]

Synthetic route is the same as shown in Example 1.

$^1$HNMR (400 MHz, DMSO-$_{d6}$), δ8.95 (d, J=8.0 Hz, 1H), 8.25~8.28 (m, 2H), 7.62~7.63 (m, 3H), 7.27 (s, 1H), 7.11 (dd, J=8.0, 2.0 Hz, 1H), 6.87 (s, 1H), 5.02~5.11 (m, J=6.0 Hz, 1H), 1.48 (d, J=6.0 Hz, 6H);

MS(ESI), m/z: 281 (M+H)$^+$.

Example 7

2-phenyl-8-propoxy-4H-pyrido[1,2-a]pyrimidin-4-one

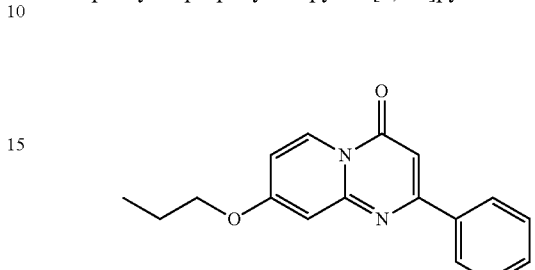

Synthetic route is the same as shown in Example 1.

$^1$HNMR (400 MHz, DMSO-$_{d6}$), δ8.95 (d, J=8.0 Hz, 1H), 8.27~8.28 (m, 2H), 7.60~7.64 (m, 3H), 7.19 (s, 1H), 7.13 (d, J=7.6 Hz, 1H), 6.88 (s, 1H), 4.30 (t, J=6.4 Hz, 2H), 1.87~1.95 (m, 2H), 1.12 (t, J=7.2 Hz, 3H);

MS(ESI), m/z: 281 (M+H)$^+$.

Example 8

3-ethyl-8-methoxy-2-phenyl-4H-pyrido[1,2-a]pyrimidin-4-one

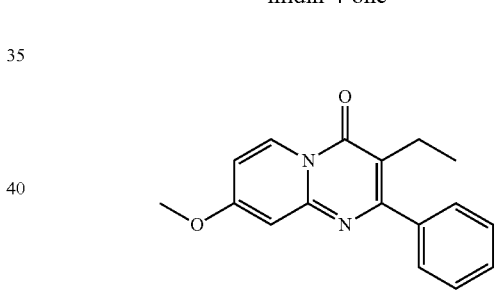

Synthetic route is the same as shown in Example 1.

$^1$HNMR (400 MHz, DMSO-$_{d6}$), δ8.84 (d, J=8.0 Hz, 1H), 7.46~7.54 (m, 5H), 7.00~7.03 (m, 2H), 3.96 (s, 3H), 2.50 (q, J=7.2 Hz, 2H), 1.07 (t, J=7.2 Hz, 3H);

MS(ESI), m/z: 280 (M+H)$^+$.

Example 9

2-phenyl-4H-pyrido[1,2-a]pyrimidin-4-one

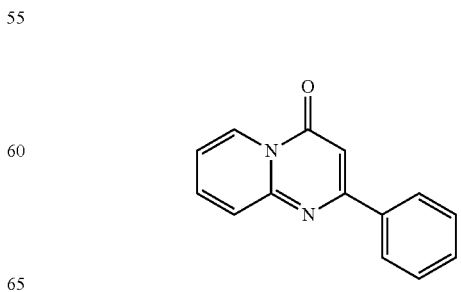

Synthetic route is the same as shown in Example 1.

¹HNMR (400 MHz, CDCl₃), δ9.02 (d, J=7.2 Hz, 1H), 8.04~8.07 (m, 2H), 7.68~7.70 (m, 2H), 7.44~7.48 (m, 3H), 7.06~7.10 (m, 1H), 6.88 (s, 1H);
MS(ESI), m/z: 223 (M+H)⁺.

Example 10

8-ethyl-2-phenyl-4H-pyrido[1,2-a]pyrimidin-4-one

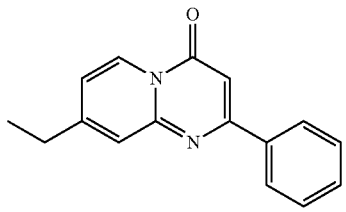 [SMILES: CCc1ccn2c(=O)cc(-c3ccccc3)nc2c1]

Synthetic route is the same as shown in Example 1.
¹HNMR (400 MHz, CDCl₃), δ8.97 (d, J=7.2 Hz, 1H), 8.07~8.09 (m, 2H), 7.60 (s, 1H), 7.49~7.50 (m, 3H), 7.01 (d, J=7.6 Hz, 1H), 6.83 (s, 1H), 2.79 (q, J=7.6 Hz, 2H), 1.35 (t, J=7.6 Hz, 3H);
MS(ESI), m/z: 251 (M+H)⁺.

Example 11

8-methoxy-2-p-tolyl-4H-pyrido[1,2-a]pyrimidin-4-one

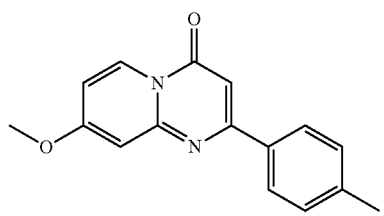

Synthetic route is the same as shown in Example 1.
¹HNMR (400 MHz, CDCl₃), δ8.92 (d, J=8.0 Hz, 1H), 7.96 (d, J=8.0 Hz, 2H), 7.29 (d, J=8.0 Hz, 2H), 7.06 (s, 1H), 6.78 (dd, J=8.0, 2.4 Hz, 1H), 6.70 (s, 1H), 3.98 (s, 3H), 2.41 (s, 3H);
MS(ESI), m/z: 267 (M+H)⁺.

Example 12

8-hydroxy-2-p-tolyl-4H-pyrido[1,2-a]pyrimidin-4-one

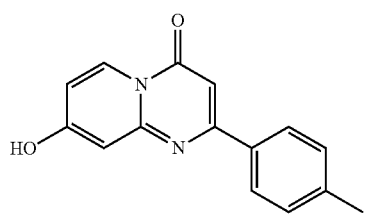 [SMILES: Cc1ccc(-c2cc(=O)n3ccc(O)cc3n2)cc1]

Synthetic route is the same as shown in Example 1.
MS(ESI), m/z: 253 (M+H)⁺.

Example 13

8-ethoxy-2-p-tolyl-4H-pyrido[1,2-a]pyrimidin-4-one

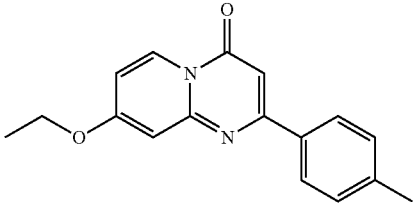 [SMILES: CCOc1ccn2c(=O)cc(-c3ccc(C)cc3)nc2c1]

Synthetic route is the same as shown in Example 1.
¹HNMR (400 MHz, CDCl₃), δ8.94 (d, J=8.0 Hz, 1H), 7.97 (d, J=8.0 Hz, 2H), 7.31 (d, J=8.0 Hz, 2H), 7.26 (s, 1H), 6.80 (dd, J=8.0, 2.0 Hz, 1H), 6.68 (s, 1H), 4.24 (q, J=7.2 Hz, 2H), 2.42 (s, 3H), 1.52 (t, J=7.2 Hz, 3H);
MS(ESI), m/z: 281 (M+H)⁺.

Example 14

2-(4-chlorophenyl)-8-methoxy-4H-pyrido[1,2-a]pyrimidin-4-one

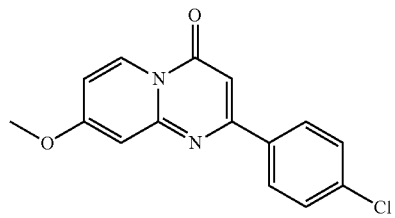 [SMILES: COc1ccn2c(=O)cc(-c3ccc(Cl)cc3)nc2c1]

Synthetic route is the same as shown in Example 1.
¹HNMR (400 MHz, CDCl₃), δ8.91 (d, J=8.0 Hz, 1H), 7.98 (d, J=8.4 Hz, 2H), 7.44 (d, J=8.4 Hz, 2H), 6.99 (s, 1H), 6.79 (dd, J=8.0, 2.0 Hz, 1H), 6.66 (s, 1H), 3.98 (s, 3H);
MS(ESI), m/z: 287 (M+H)⁺.

Example 15

2-(4-chlorophenyl)-8-hydroxy-4H-pyrido[1,2-a]pyrimidin-4-one

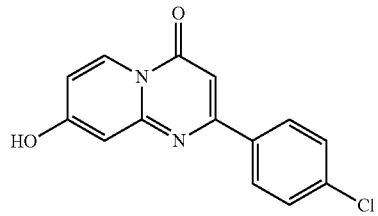 [SMILES: O=c1cc(-c2ccc(Cl)cc2)nc2cc(O)ccn12]

Synthetic route is the same as shown in Example 1
MS(ESI), m/z: 273 (M+H)⁺. .

Example 16

2-(3-chlorophenyl)-8-methoxy-4H-pyrido[1,2-a]pyrimidin-4-one

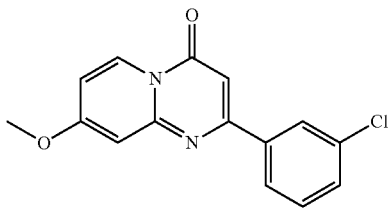 [SMILES: COc1ccn2c(=O)cc(-c3cccc(Cl)c3)nc2c1]

Synthetic route is the same as shown in Example 1.
¹HNMR (400 MHz, CDCl₃), δ8.88 (d, J=7.2 Hz, 1H), 8.06 (s, 1H), 7.85 (dd, J=7.2, 1.2 Hz, 1H), 7.36-7.42 (m, 2H), 6.96 (s, 1H), 6.77 (d, J=8.0 Hz, 1H), 6.65 (d, J=1.2 Hz, 1H), 3.96 (s, 3H);
MS(ESI), m/z: 287 (M+H)⁺.

Example 17

2-(4-chlorophenyl)-8-ethoxy-4H-pyrido[1,2-a]pyrimidin-4-one

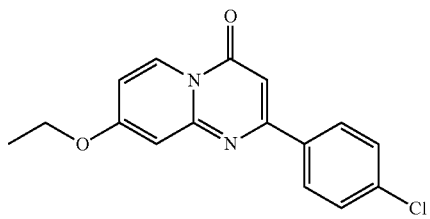 [SMILES: CCOc1ccn2c(=O)cc(-c3ccc(Cl)cc3)nc2c1]

Synthetic route is same as shown in Example 1.
¹HNMR (400 MHz, CDCl₃), δ9.05 (d, J=8.0 Hz, 1H), 8.12 (d, J=8.8 Hz, 2H), 7.58 (d, J=8.4 Hz, 2H), 7.38 (s, 1H), 6.93 (dd, J=8.0, 2.0 Hz, 1H), 6.77 (s, 1H), 4.36 (q, J=6.8 Hz, 2H), 1.64 (t, J=6.8 Hz, 3H);
MS(ESI), m/z: 301 (M+H)⁺.

Example 18

2-(2-chlorophenyl)-8-methoxy-4H-pyrido[1,2-a]pyrimidin-4-one

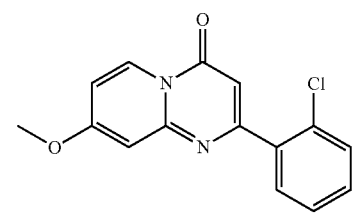 [SMILES: COc1ccn2c(=O)cc(-c3ccccc3Cl)nc2c1]

Synthetic route is the same as shown in Example 1.
¹HNMR (400 MHz, CDCl₃), δ8.96 (d, J=8.0 Hz, 1H), 7.56~7.59 (m, 1H), 7.45~7.48 (m, 1H), 7.34~7.37 (m, 2H), 6.98 (d, J=2.0 Hz, 1H), 6.82 (dd, J=7.6, 2.4 Hz, 1H), 6.54 (s, 1H), 3.95 (s, 3H);
MS(ESI), m/z: 287 (M+H)⁺.

Example 19

8-ethyl-3-methyl-2-phenyl-4H-pyrido[1,2-a]pyrimidin-4-one

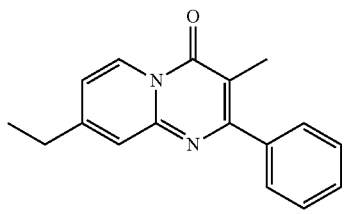 [SMILES: CCc1ccn2c(=O)c(C)c(-c3ccccc3)nc2c1]

Synthetic route is same as shown in Example 1.
¹HNMR (400 MHz, DMSO-$d_6$), δ8.85 (d, J=7.2 Hz, 1H), 7.59~7.61 (m, 2H), 7.47~7.52 (m, 3H), 7.45 (s, 1H), 7.23 (dd, J=7.2, 1.6 Hz, 1H), 2.74 (q, J=7.2 Hz, 2H), 2.15 (s, 3H), 1.25 (t, J=7.2 Hz, 3H);
MS(ESI), m/z: 265 (M+H)⁺.

Example 20

8-ethoxy-3-methyl-2-phenyl-4H-pyrido[1,2-a]pyrimidin-4-one

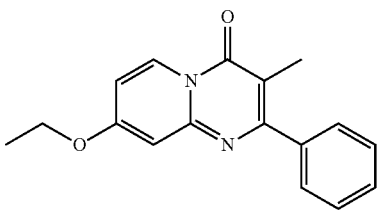 [SMILES: CCOc1ccn2c(=O)c(C)c(-c3ccccc3)nc2c1]

Synthetic route is the same as shown in Example 1.
¹HNMR (400 MHz, CDCl₃), δ9.02 (d, J=7.6 Hz, 1H), 7.67 (d, J=8.0 Hz, 2H), 7.54~7.60 (m, 3H), 7.35 (d, J=0.8 Hz, 1H), 6.91 (dd, J=8.0, 1.6 Hz, 1H), 4.29 (q, J=6.8 Hz, 2H), 2.32 (s, 3H), 1.59 (t, J=6.8 Hz, 3H);
MS(ESI), m/z: 281 (M+H)⁺.

Example 21

8-hydroxy-3-methyl-2-phenyl-4H-pyrido[1,2-a]pyrimidin-4-one

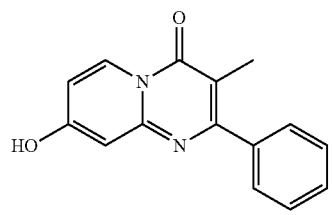 [SMILES: Cc1c(-c2ccccc2)nc2cc(O)ccn2c1=O]

Synthetic route is the same as shown in Example 1.
¹HNMR (400 MHz, DMSO-$d_6$), δ9.00 (d, J=7.6 Hz, 1H), 7.60~7.67 (m, 5H), 7.21 (dd, J=7.6, 2.4 Hz, 1H), 7.08 (d, J=2.4 Hz, 1H), 2.02 (s, 3H);
MS(ESI), m/z: 253 (M+H)⁺.

Example 22

6-methyl-2-phenyl-4H-pyrido[1,2-a]pyrimidin-4-one

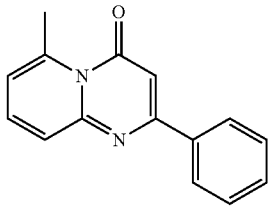 [SMILES: Cc1cccc2nc(-c3ccccc3)cc(=O)n12]

Synthetic route is the same as shown in Example 1.
$^1$HNMR (400 MHz, CDCl$_3$), δ8.06 (t, 2H), 7.42~7.56 (m, 5H), 6.72 (s, 1H), 6.65 (d, J=6.8 Hz, 1H), 3.08 (s, 3H);
MS(ESI), m/z: 237 (M+H)$^+$.

Example 23

7-methyl-2-phenyl-4H-pyrido[1,2-a]pyrimidin-4-one

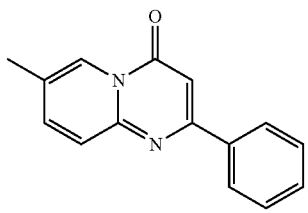 [SMILES: Cc1ccc2nc(-c3ccccc3)cc(=O)n2c1]

Synthetic route is the same as shown in Example 1.
$^1$HNMR (400 MHz, CDCl$_3$), δ8.89 (s, 1H), 8.07~8.09 (m, 2H), 7.77 (d, J=9.2 Hz, 1H), 7.65 (dd, J=9.2, 1.6 Hz, 1H), 7.49~7.52 (m, 3H), 6.88 (s, 1H), 2.45 (s, 3H);
MS(ESI), m/z: 237 (M+H)$^+$.

Example 24

8-methyl-2-phenyl-4H-pyrido[1,2-a]pyrimidin-4-one

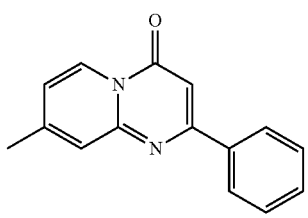 [SMILES: Cc1ccn2c(=O)cc(-c3ccccc3)nc2c1]

Synthetic route is same as shown in Example 1.
$^1$HNMR (400 MHz, CDCl$_3$), δ8.96 (d, J=7.2 Hz, 1H), 8.07~8.09 (m, 2H), 7.65 (s, 1H), 7.48~7.50 (m, 3H), 6.98 (d, J=7.2 Hz, 1H), 6.82 (s, 1H), 2.50 (s, 3H);
MS(ESI), m/z: 237 (M+H)$^+$.

Example 25

9-methyl-2-phenyl-4H-pyrido[1,2-a]pyrimidin-4-one

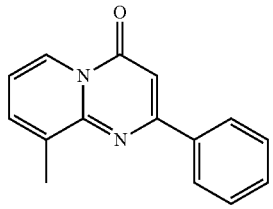 [SMILES: Cc1cccn2c(=O)cc(-c3ccccc3)nc12]

Synthetic route is the same as shown in Example 1.
$^1$HNMR (400 MHz, CDCl$_3$), δ8.97 (d, J=7.2 Hz, 1H), 8.16~8.18 (m, 2H), 7.61 (d, J=6.8 Hz, 1H), 7.50~7.51 (m, 3H), 7.02~7.06 (t, 1H), 6.95 (s, 1H), 2.71 (s, 3H);
MS(ESI), m/z: 237 (M+H)$^+$.

Example 26

8-(3-morpholinopropoxy)-2-phenyl-4H-pyrido[1,2-a]pyrimidin-4-one

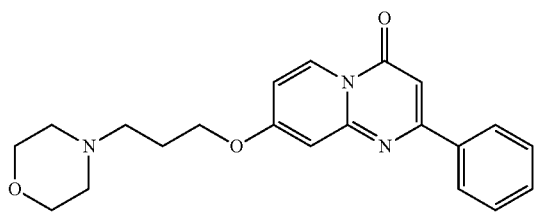 [SMILES: O=c1cc(-c2ccccc2)nc2cc(OCCCN3CCOCC3)ccn12]

Synthetic route is the same as shown in Example 1.
$^1$HNMR (400 MHz, CDCl$_3$), δ8.79 (d, J=7.6 Hz, 1H), 8.13~8.14 (m, 2H), 7.45~7.49 (m, 3H), 7.05 (s, 1H), 6.97 (d, J=7.6 Hz, 1H), 6.73 (s, 1H), 4.23 (t, J=5.6 Hz, 2H), 3.51~3.55 (m, 4H), 2.28~2.41 (m, 6H), 1.90 (t, J=6.4 Hz, 2H);
MS(ESI), m/z: 366 (M+H)$^+$.

Example 27

8-chloro-2-phenyl-4H-pyrido[1,2-a]pyrimidin-4-one

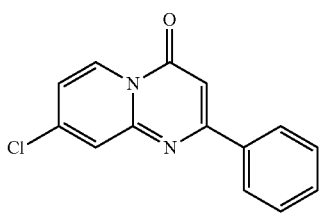 [SMILES: O=c1cc(-c2ccccc2)nc2cc(Cl)ccn12]

Synthetic route is the same as shown in Example 1.
$^1$HNMR (400 MHz, CDCl$_3$), δ8.98 (d, J=7.2 Hz, 1H), 8.07~8.08 (m, 2H), 7.82 (s, 1H), 7.50~7.52 (m, 3H), 7.09 (d, J=7.6 Hz, 1H), 6.88 (s, 1H);
MS(ESI), m/z: 257 (M+H)$^+$.

Example 28

Current example illustrates that the compounds mentioned in this invention (such as the compound in Example 10, also named DK45, 8-ethyl-2-phenyl-4H-pyrido[1,2-a]pyrimidin-4-one) and other compounds with core structure of Formula VIII such as the compound of Example 1, also named DK36, 8-methoxy-2-phenyl-4H-pyrido[1,2-a]pyrimidin-4-one, and the compound of Example 6, also named DK41, 8-isopropoxy-2-phenyl-4H-pyrido[1,2-a]pyrimidin-4-one, can effectively enhance the expression of reporter genes modulated by ERRα in 293 FT cell, therefore these compounds can effectively enhance the function of ERRα.

To test the effect of the compounds on ERR and other nuclear hormone receptors, 293 FT cells were transiently transfected with expression vectors for the receptors along with appropriate reporter constructs according to methods known in the art. Suitable reporter gene constructs are well known to skilled workers in the fields of biochemistry and molecular biology. Other vectors known in the art can be used in the methods of the present invention.

GAL4 fusions containing receptor ligand binding domain fragments were constructed by fusing human ERRα, human ERRβ and murine ERRγ ligand binding domain sequences to the C-terminal end of the yeast GAL4 DNA binding domain (amino acids 1-147 accession X85976) to form the expression vectors GAL-hERRα, GAL-L-hERRβ and Gal-mERRγ, respectively. pGAL is a control containing the yeast GAL4 DNA binding domain without receptor sequences. CMV-PGC-1α contains and expressed the PGC-1α coding sequences derived from PGC-1α (accession NM.sub.--008904).

293 FT cells for the activation assays were grown in Dulbecco's modified Eagle's medium supplemented with 10% resin charcoal-stripped fetal bovine serum at 37° C. in 5% $CO_2$. One day prior to transfection, cells were plated to 50-80% confluence using phenol red free DMEM-FBS. The cells were transiently transfected by lipofection but other methods of transfection of DNA into cells can be utilized without deviating from the spirit of the invention. Luciferase reporter construct UASgx4-TK-Luc and cytomegalovirus-driven expression vector p-GAL, GAL-hERRα, GAL-L-hERRβ or Gal-mERRγ were added with CMV-PGC-1α. The cells were treated for approximately 24 hours with phenol red free DMEM-FBS containing 0.01% DMSO (control) or 0.01% DMSO with increasing concentrations of DK compounds.

The compound of Example 10, also named DK45, 8-ethyl-2-phenyl-4H-pyrido[1,2-a]pyrimidin-4-one and other compounds with core structure of Formula VIII such as the compound of Example 1, also named DK36, 8-methoxy-2-phenyl-4H-pyrido[1,2-a]pyrimidin-4-one, and compound of Example 6, also named DK41, 8-isopropoxy-2-phenyl-4H-pyrido[1,2-a]pyrimidin-4-one, dose-dependently enhances the activity of GAL-hERRα on reporter construct UASgx4-TK-Luc in the presence of CMV-PGC-1α. (FIG. 1). These suggested that these compounds functioned to increase the activity of ERRα.

Example 29

Current example illustrates that compounds mentioned in this invention such as DK45 can effectively enhance the expression of PGC1α-promoter reporter gene and PDK4-promoter reporter gene in HeLa cell.

HeLa were transiently transfected with the pGL3-promoter (Promega) derivative pGL3-PGC1α-promoter or PDK4-Promega and expression vector for ERRα. The Renilla-Luciferase pRL-CMV Vector (Promega) was included as a control for transfection efficiency. The full length human ERRα was cloned into the expression vector pCMV. The pGL3-PGC1α-promoter or PDK4-promoter was generated by cloning an insert derived from a PCR reaction using human genomic DNA as template and primers based on the 2.6 kbp upstream sequence of the PGC1α transcriptional start site.

HeLa cells for the activation assays were grown in Dulbecco's modified Eagle's medium supplemented with 10% fetal bovine serum at 37° C. in 5% $CO_2$. One day prior to transfection, cells were plated to 50-80% confluence using DMEM-FBS. The cells were transiently transfected by lipofection but other methods of transfection of DNA into cells can be utilized without deviating from the spirit of the invention. Luciferase reporter construct pGL3-PGC1α-promoter or PDK4-promoter and cytomegalovirus-driven expression vector pCMV or pCMV-hERRα were added. The cells were treated for approximately 24 hours with DMEM-FBS containing 0.01% DMSO (control) or 0.01% DMSO with 10 uM DK45 compound.

Figure 2:
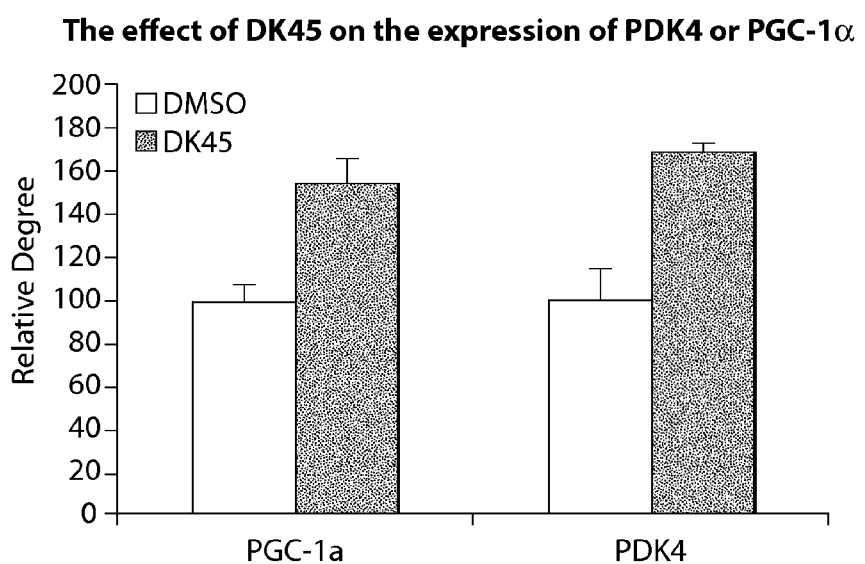
FIG. 2 is a diagram showing the effect of DK45 on the reporter gene expression of the promoter PGC1α driven by ERRα.

The enhancement of the PGC1α-promoter reporter gene and PDK4-promoter reporter gene driven by ERRα was observed for the compound DK45 (FIG. 2).

Example 30

Current example illustrates that compounds mentioned in this invention such as DK45 can effectively improve glucose tolerance in high-fat-diet mice.

Seven weeks old male C57BL/J6 mice were either fed chow diet or a high-fat-diet with 60% calories from lard for 10 weeks. Compounds were administered to animals by gavage for two weeks at different doses. Four groups of animals (n=5) were administered with either vehicle, 5 mg/kg/day rosiglitazone, or 5 mg/kg/day DK45. Animals were fasted for 5 h, and then orally fed glucose. Blood samples were withdrawn at time 0, 15, 30, 60 and 120 min. Blood glucose level was measured by monitor (Accu-chek Advantage, Roche). The changes in blood glucose level were plotted against time and the areas under the curve were calculated for the different groups.

Figure 3:
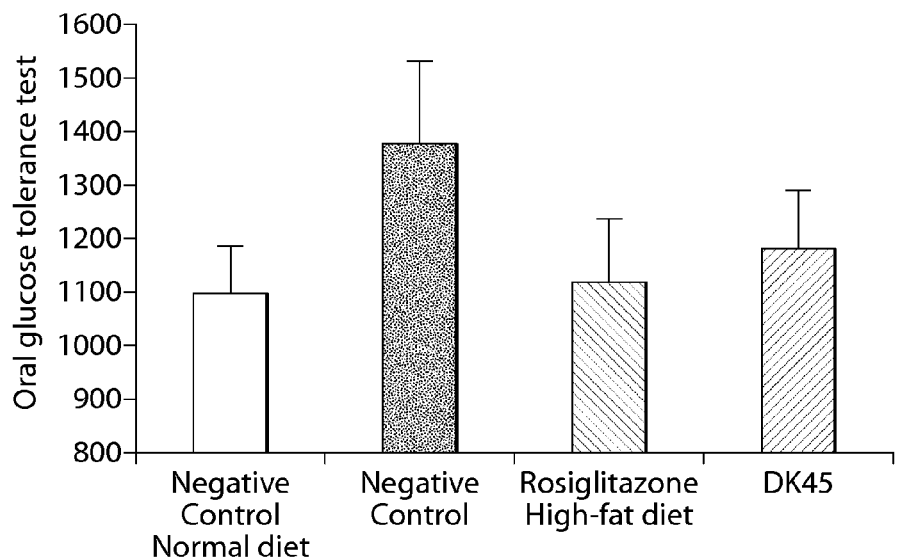
FIG. 3 is a diagram showing the effect of DK45 on the oral glucose tolerance.
Figure 4:
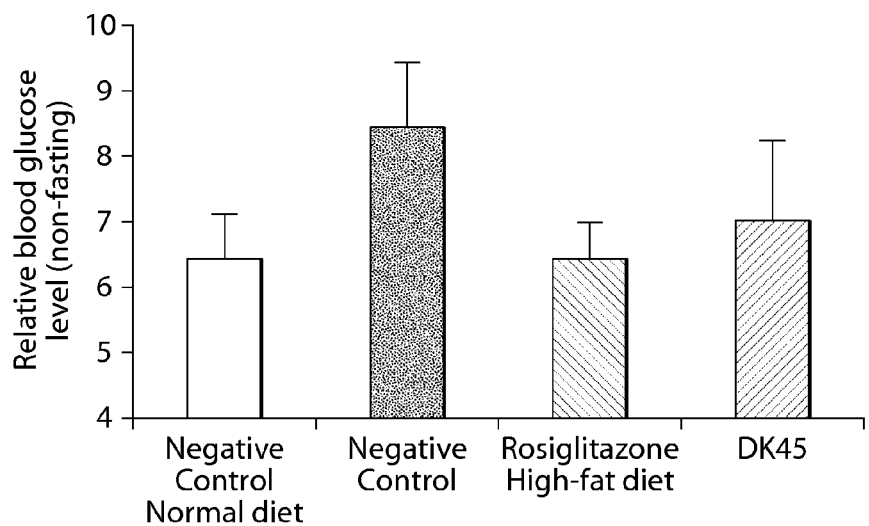
FIG. 4 is a diagram showing the effect of DK45 on the blood glucose level (without fasting)

Compared to positive control rosiglitazone given at 5 mg/kg/day, DK45 at 5 mg/kg/day reduced the area under the curve of the oral glucose tolerance test, indicating that ERRα agonists DK45 improve glucose tolerance in vivo (FIG. 3). Non-fasting treatments also suggest that DK45 at 5 mg/kg/day reduced the blood glucose levels.

In addition, insulin resistance test was administered. Animals were fasted for 5 h, and then injected insulin (0.75 IU/kg). Blood samples were withdrawn at time 0, 15, 30, 60 and 120 min. Blood glucose level was measured by monitor (Accu-chek Advantage, Roche). The changes in blood glucose level were plotted against time and the areas under the curve were calculated for the different groups.

Figure 5:
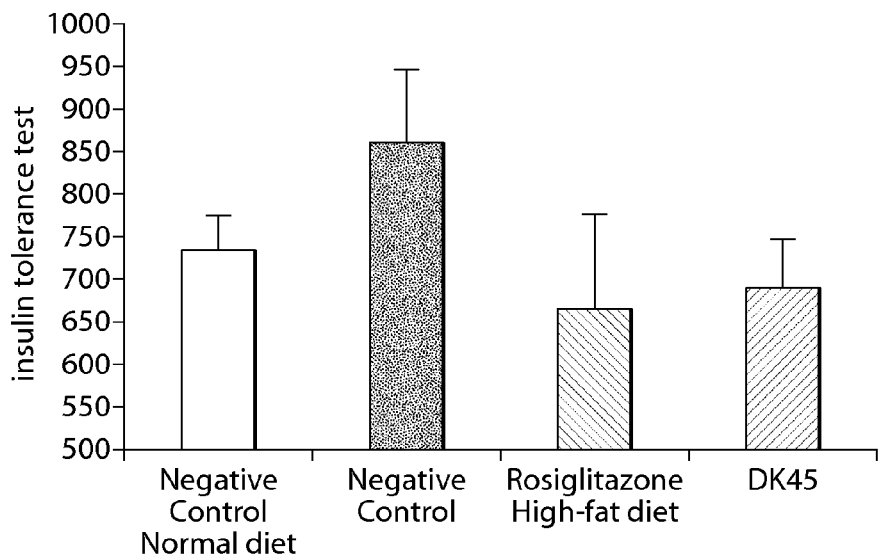
FIG. 5 is a diagram showing the effect of DK45 on the insulin tolerance.
Figure 6:
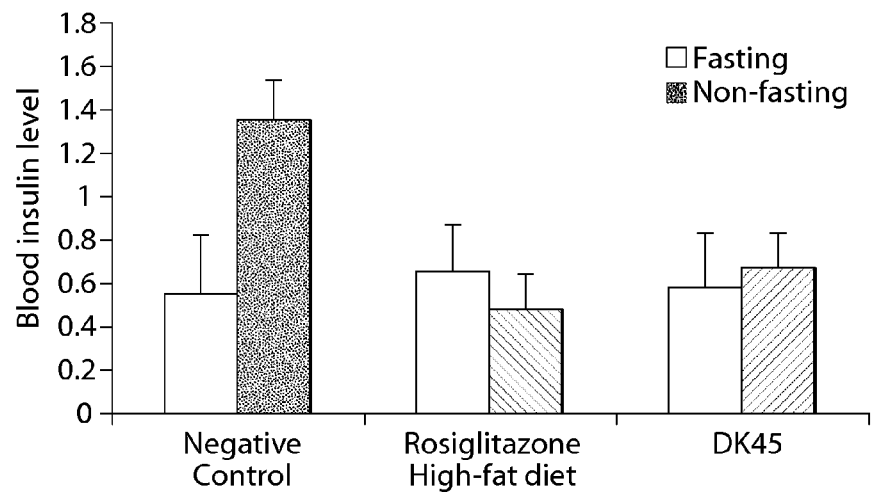
FIG. 6 is a diagram showing the effect of DK45 on the blood insulin level.

Compared to positive control rosiglitazone given at 5 mg/kg/day, DK45 at 5 mg/kg/day reduced the area under the curve of the insulin resistance test, indicating that ERRα agonists DK45 improve insulin sensitivity in vivo (FIG. 5). The blood insulin levels of fasting and non-fasting treatments also indicate that DK45 at 5 mg/kg/day reduced the blood insulin levels of non-fasting treatments (FIG. 6).

Figure 7:
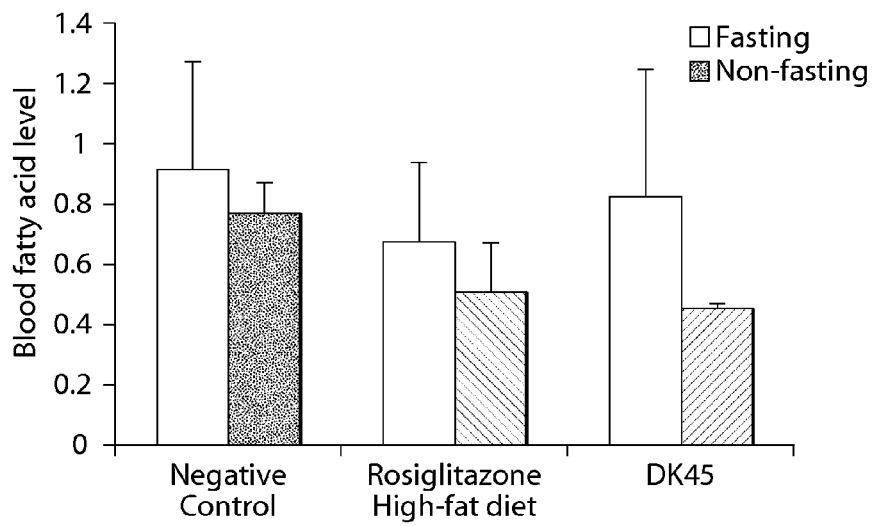
FIG. 7 is a diagram showing the effect of DK45 on the blood fatty acid level.
Figure 8:
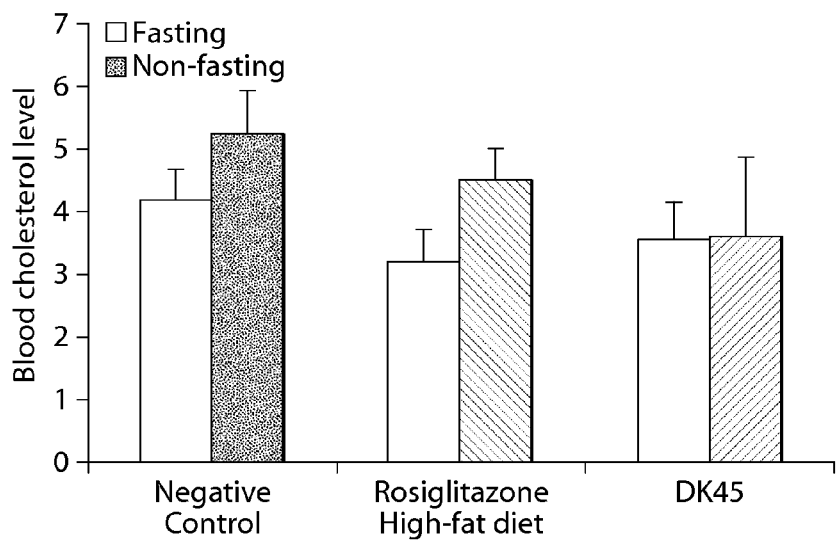
FIG. 8 is a diagram showing the effect of DK45 on the total blood cholesterol level.
Figure 9:
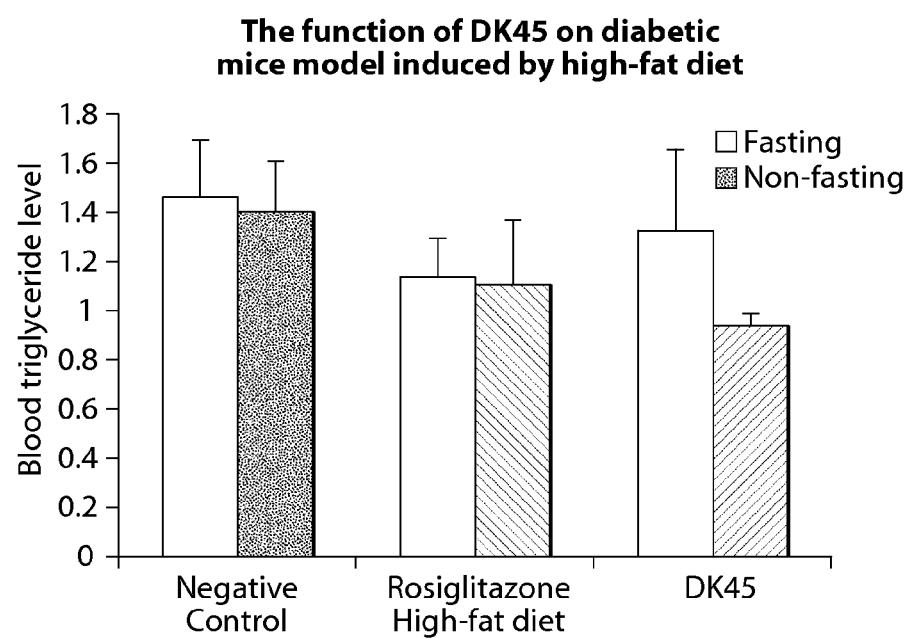
FIG. 9 is a diagram showing the effect of DK45 on the blood triglyceride.

Moreover, DK45 at 5 mg/kg/day reduced serum free fatty acid (FIG. 7), cholesterol (FIG. 8), and triglyceride levels (FIG. 9) of non-fasting treatments.

What is claimed is:

1. The compound 8-ethyl-2-phenyl-4H-pyrido[1,2-a]pyrimidin-4-one or pharmaceutically acceptable salt or stereoisomer thereof:

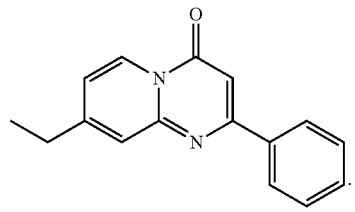 [SMILES: CCc1ccn2c(=O)cc(-c3ccccc3)nc2c1]

2. A pharmaceutical composition comprising a compound or a pharmaceutically acceptable salt or stereoisomer thereof according to claim 1 and a pharmaceutically acceptable carrier.

3. A method of treating a metabolic disease, the method comprising administering an effective amount of compound or a pharmaceutically acceptable salt or stereoisomer thereof according to claim 1 to a patient in need thereof, thereby treating the metabolic disorder in the patient wherein the metabolic disease is (1) Type II diabetes; (2) hyperglycemia; (3) reduced glucose tolerance; (4) insulin resistance; (5) obesity; (6) abnormal fat metabolism; (7) dyslipidemia; (8) hyperlipidemia; (9) hypertriglyceridemia; (10) hypercholesterolemia; (11) low levels of HDL; (12) high levels of LDL; (13) atherosclerosis; (14) vascular restenosis; (15) central obesity; (16) metabolic syndrome; or (17) fatty liver.

* * * * *